United States Patent [19]
Guindon

[11] Patent Number: 5,242,946
[45] Date of Patent: Sep. 7, 1993

[54] TREATING HERPES VIRAL INFECTIONS
[75] Inventor: Yvan Guindon, Montreal, Canada
[73] Assignee: Bio-Mega, Inc., Laval, Canada
[21] Appl. No.: 830,019
[22] Filed: Jan. 31, 1992

Related U.S. Application Data
[63] Continuation of Ser. No. 425,523, Oct. 23, 1989, abandoned.

[30] Foreign Application Priority Data
Oct. 27, 1988 [CA] Canada .................................. 581457

[51] Int. Cl.$^5$ .............................................. A61K 31/21
[52] U.S. Cl. ...................................... 514/510; 514/532; 514/533; 514/548; 514/934
[58] Field of Search ............... 514/532, 533, 548, 934, 514/510

[56] References Cited
U.S. PATENT DOCUMENTS
4,466,981  8/1984  Jones et al. .......................... 424/311
4,593,120  6/1986  Jones et al. .......................... 560/107

FOREIGN PATENT DOCUMENTS
1243401  8/1971  United Kingdom .

OTHER PUBLICATIONS
M. Nahata, "Antiviral Drugs: Pharmacokinetics, Adverse Effects and Therapeutic Use", J. Pharm. Technol 3, 100 (1987).
Jones et al, "Topical Nonsteroidal Antipsoriatic Agents, 1, 1,2,3,4–Tetraoxygenated Naphthalene Derivatives", J. Med. Chem. 29, 1504 (1986).
Stebaeva et al, Mechanism of the antiherpetic effect of bonaphthon, Chem. Abstracts 83: 179724j (1980).

Primary Examiner—Frederick E. Waddell
Assistant Examiner—Russell Travers
Attorney, Agent, or Firm—David E. Frankhouser; Daniel Reitenbach; Mary-E. M. Timbers

[57] ABSTRACT

A group of known naphthalene derivatives have been found to be useful for preventing or relieving herpes viral infections.

10 Claims, 1 Drawing Sheet

TREATING HERPES VIRAL INFECTIONS

This is a continuation of application Ser. No. 425,523, filed Oct. 23, 1989, now abandoned.

FIELD OF THE INVENTION

This invention relates to a method of preventing or relieving herpes viral infections in a mammal by administering thereto certain naphthalene derivatives. The invention also relates to a cosmetic formulation of the naphthalene derivatives and to the use of the formulation to prevent the outbreak of herpetic lesions of the skin.

BACKGROUND OF THE INVENTION

Since time immemorial, herpes viral infections have been a scourge of mankind and many important domestic animals. The herpes family of virus includes herpes virus simplex (types 1 and 2) responsible for cold sores and genital lesions, respectively; varicella zoster virus which causes chicken pox and shingles; and the Epstein-Barr virus which causes infectious mononucleosis. Although some significant advances have been made in the last decade in antiviral therapy, the need for effective, safe therapeutic agents for treating herpes viral infections continues to exist. For a recent review of current therapeutic agents in this area, see M. C. Nahata, "Antiviral Drugs: Pharmacokinetics, Adverse Effects and Therapeutic Use", J. Pharm. Technol., 3, 100 (1987).

It has now been found that a group of naphthalene derivatives, having a wide margin of safety, are useful for combatting herpes viral infections. The naphthalene derivatives are known having been described previously as antipsoriatic agents, see G. H. Jones et al., U.S. Pat. No. 4,466,981, issued Aug. 21, 1984 and U.S. Pat. No. 4,593,120, issued Jun. 3. 1986. See also G. H. Jones et al., J. Med. Chem. 29, 1504 (1986).

Accordingly, the present invention provides a well tolerated and effective means for preventing or relieving herpes viral infections.

The association of antiviral activity with the above-noted napththalene derivatives is an unusual finding. On a structural basis, it represents a departure from the chemical structures of compounds usually associated with antiviral activity, such as purine and pyrimidine nucleosides, 1-adamatanamine, particular interferons, etc. Two naphthalene derivatives, nevertheless, have previously been reported to have antiviral properties. The two naphthalene derivatives are 1,2,3,4-napththalenetetrone, M. Y. Kraft et al., UK patent 1,243,401, Aug. 18, 1971, and 6-bromo-1,2-naphthalenedione, L. F. Stebaeva et al., Farmakol. Toksikol. (Moscow), 43, 609 (1980); Chem. Abstr., 93, 179724j (1980). The naphthalene derivatives of the present application are distinguished readily from the latter two naphthalene derivatives by marked structural differences arising from the substituents on, and oxidation levels of, their bicyclic structures.

SUMMARY OF THE INVENTION

Disclosed herein is a method for preventing or relieving herpes viral infections in a mammal. The method comprises administering to the mammal an antiherpes virally effective amount of a naphthalene derivative of formula 1

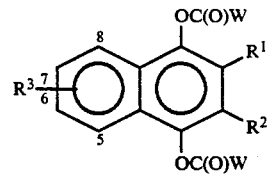

wherein:
$R^1$ and $R^2$ are lower alkoxy or lower alkylthio;
$R^3$ is hydrogen, lower alkyl, lower alkoxy, optionally substituted phenyl, optionally substituted phenyl lower alkyl, optionally substituted phenyl alkoxyl, amino, lower alkylemino, lower dialkylamino, halo, cyano, or $S(O)_nR$ wherein R is lower alkyl; optionally substituted phenyl; optionally substituted phenyl lower alkyl; or heterocyclic aryl or three to nine ring atoms containing one or two heteroatoms selected from the group consisting of nitrogen, oxygen and sulfur wherein the ehterocyclic aryl is optionally substituted by one or more substitutents selected from the group consisting of lower alkyl, lower alkoxy, halo and cyano or the therapeutically acceptable acid addition salts thereof; and n is 0, 1 or 2; and W is alkyl of one to seven carbon atoms.

A preferred group of the derivatives for effecting the method of this invention is represented by formula 1 wherein $R^1$, $R^2$ and W are as defined hereinabove and $R^3$ is hydrogen, lower alkyl, lower alkoxy, phenyl optionally substituted by one or more lower alkyl, lower alkoxy, halo, lower acyl, lower acyloxy, cyano, nitro or lower acylamino, phenyl lower alkyl optionally substituted by one or more lower alkyl, lower alkoxy, halo, lower acyl, lower acyloxy, cyano, nitro or lower acylamino, phenyl lower alkoxy optionally substitued by one or more lower alkyl, lower alkoxy, halo, lower acyl, lower acyloxy, cyano, nitro or lower acylamino, amino, lower alkylamino, lower dialkylamino, halo, cyano or $S(O)_nR$ wherein R is lower alkyl; phenyl optionally substituted by one or more lower alkyl, lower alkoxy, halo, lower acyl, lower acyloxy, cyano, nitro or lower acylamino; phenyl lower alkyl optionally substituted by one or more lower alkyl, lower alkoxy, halo, lower acyl, lower acyloxy, cyano, nitro or lower acylamino; or heterocyclic aryl selected from the group consisting of thiapyranyl, benzothiapyranyl, furyl, pyrrolyl, imidazolyl, pyrazolyl, pyridinyl, pyrimidinyl, indolyl, quinolinyl and indazolyl wherein the heterocyclic aryl is optionally substituted by one or more substituents selected from the group consisting of lower alkyl, lower alkoxy, halo and cyano or the therapeutically acceptable acid addition salts thereof; and n is 0, 1 or 2.

A more preferred group of the derivatives for effecting the method is represented by formula 1a

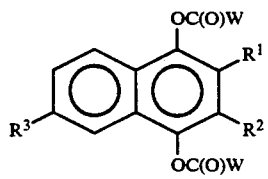

wherein $R^1$, $R^2$ and $R^3$ and W are as defined hereinabove.

A still more preferred group of the derivatives for effecting the method is represented by formula 1a wherein $R^1$ and $R^2$ are lower alkoxy, and $R^3$ and W are as defined hereinabove.

Another still more preferred group of the derivatives for effecting the method is represented by formula 1a wherein $R^1$ and $R^2$ are lower alkoxy, $R^3$ is hydrogen, bromo, chloro, fluoro or cyano, and W is as defined hereinabove.

A most preferred group of the derivatives for effecting the method is represented by formula 1a wherein $R^1$ and $R^2$ are lower alkoxy of one to four carbon atoms, $R^3$ is bromo, chloro, fluoro, cyano, methoxy, ethoxy, propoxy, 1-methylethoxy, butoxy or 2-methylpropoxy, and W is an alkyl of one to five carbon atoms.

In another aspect of the present invention, a cosmetic composition is provided. The cosmetic composition comprises a naphthalene derivative of formula 1, or a therapeutically acceptable salt thereof, and a physiologically acceptable carrier. The cosmetic composition is used to prevent the outbreak of herpetic lesions of the skin.

DETAILED DESCRIPTION OF THE INVENTION

Figure 1:
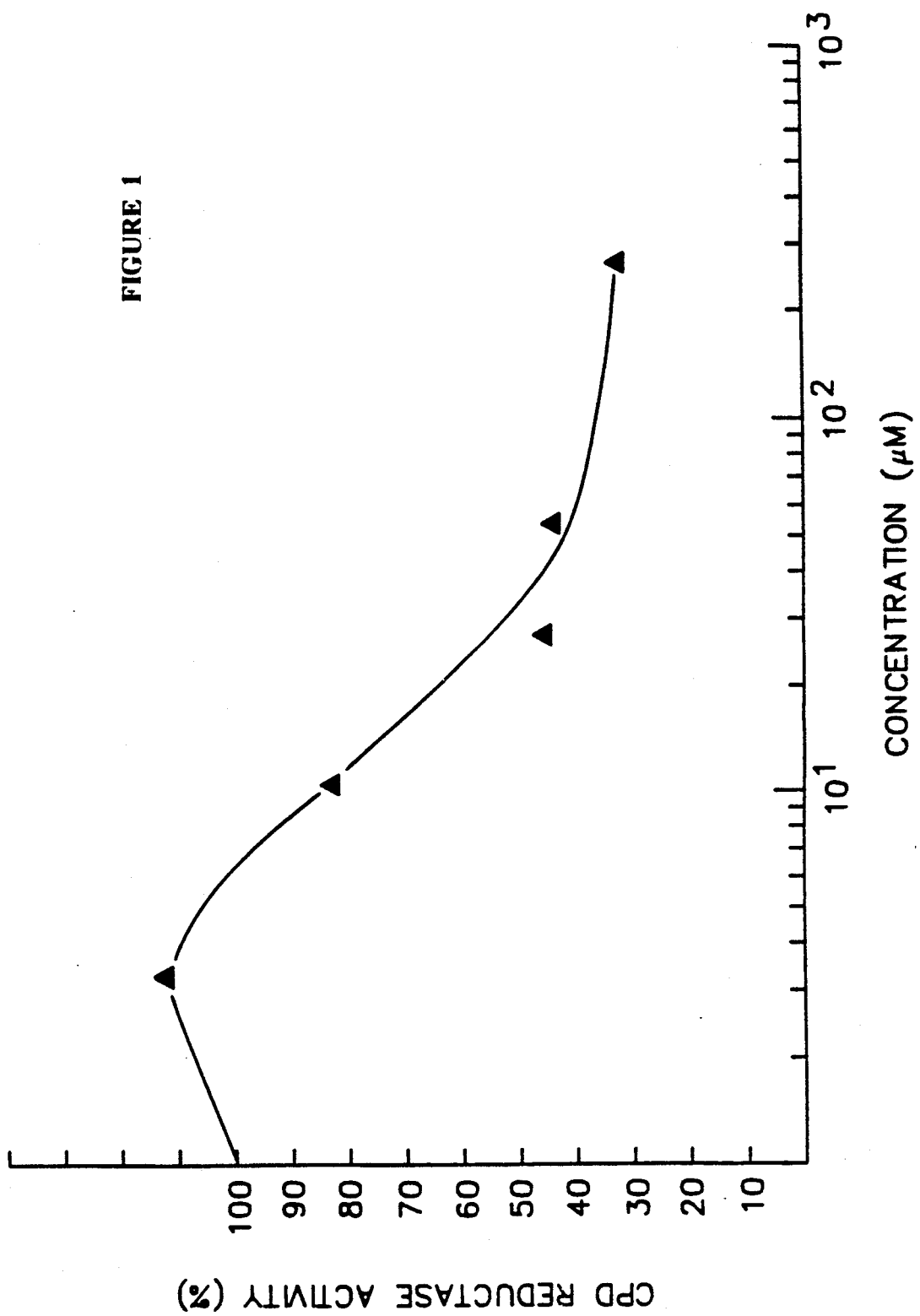
FIG. 1 shows the progressively greater inhibitory effect of increasing concentrations of the naphthalene derivative of formula 1 in which $R^1$ and $R^2$ are each methoxy, $R^3$ is 6-chloro and W is methyl on herpes simplex virus (type 1) ribonucleotide reductase activity. (Note: lonapalene is the generic name for the last named naphthalene derivative.)

For convenience, the naphthalene derivatives of formula 1 are designated hereafter simply as "naphthalenes".

The term "alkyl" as used herein means an alkyl radical containing one to seven carbon atoms and includes straight chain as well as branched chain radicals. Illustrative of such radicals are methyl, ethyl, propyl, 1-methylethyl, and heptyl. The term "lower alkyl" means an alkyl radical containing one to six carbon atoms and includes straight chain and branched chain alkyl radicals. Examples of lower alkyl radicals are methyl, ethyl, propyl, butyl, hexyl, 1-methylethyl, 2-methylpropyl and 1,1-dimethylethyl.

The term "phenyl lower alkyl" means an optionally substituted phenyl ring attached to an alkylene chain of one to six carbon atoms.

The term "lower alkoxyl" means a straight or branched chain aliphatic group of one to six carbon atoms having bonded thereto an oxygen moiety. Preferred lower alkoxy radicals have one to four carbon atoms. Examples of "lower alkoxy" are methoxy, ethoxy, propoxy, 1-methlethoxy and butoxy.

The term "phenyl lower alkoxy" means a phenyl ring attached to an alkylene chain of one to six carbon atoms having bonded thereto an oxygen atom. Examples of "phenyl lower alkoxy" are benzyloxy, 4-chlorophenylethoxy and phenylpropoxy.

The term "lower alkylthio" means a straight or branched chain aliphatic group of one to six carbon atoms having bonded thereto a sulfur moiety. Examples of "lower alkylthio" are methylthio, ethylthio, propylthio, butylthio and 2-methylpropylthio.

Optionally substituted phenyl refers to a phenyl ring optionally substituted by one or more substituents selected from the group consisting of lower alkyl, lower alkoxy, halo, lower acyl, lower acyloxy, cyano, nitro, amino and lower acylamino.

The term "halo" refers to fluoro, chloro and bromo. The term "cyano" refers to the group —CN. The term "amino" refers to the group —NH$_2$.

The term "lower alkylamino" refers to an amino group substituted by lower alkyl as is defined above. Examples of "lower alkylamino" are methylamino, ethylamino and butylamino.

The term "lower dialkylamino" refers to an amino group substituted by two lower alkyl groups. Examples of "lower dialkylamino" are dimethylamino, dipropylamino and methylethlamino.

The term "lower acyl" when used alone or in combination refers to the group $R^4C(O)$— wherein $R^4$ is a lower alkyl group of one to six carbon atoms or an optionally substituted phenyl group. Examples of "lower acyl" are acetyl, propanoyl, butanoyl and benzoyl.

The term "heterocyclic aryl" is defined as those cyclic aromatic compounds having 3 to 9 ring carbon atoms and having one or two heteroatoms in the ring selected from the group consisting of nitrogen, oxygen and sulfur. Example of such include the groups thiapyranyl, benzothiapyranyl, furyl, pyrrolyl, imidazolyl, pyrazolyl, pyridinyl, pyrimidinyl, indolyl, quinolinyl, indazolyl and the like. These heterocyclic aryls may be optionally substituted with halo, lower alkyl, cyano and lower alkoxy.

Term "therapeutically acceptable acid addition salts", as used in the case of the various $R^3$ radicals containing basic, heterocyclic aryl substituents, means those non- toxic therapeutically acceptable acid additional salts which do not adversely affect the pharmaceutical properties of the parent compounds. With respect to these addition salts, suitable inorganic anions included, for example, chloride, bromide, iodide, sulfate, phosphate, nitrate, and the like. Suitable organic anions include, for example, acetate, benzoate, lactate, propionate, butyrate, valerate, tartrate, maleate, fumarate, citrate, succinate, tosylate, ascorbate, nicotinate, adipate and gluconate.

The term "physiologically acceptable carrier" as used herein means an acceptable cosmetic vehicle suitable for topical application to the skin of one or more non-toxic excipients which do not react with, or reduced the effectiveness of, the active ingredient contained therein.

The term "effective amount" means a predetermined antiviral amount of the antiviral agent which is effective against the viral organism in vivo.

The naphthalenes of formula 1 can be prepared by previously disclosed procedures described by G. H. Jones et al. in U.S. Pat. No. 4,466,981 and 4,593,120 and by G. H. Jones et al. in the J. Med. Chem. publication, cited hereinabove. The disclosures of these two U.S. patents and the J. Med. Chem. publication are herein incorporated by reference.

The antiviral activity of the naphthalenes of formula 1 can be demonstrated by biochemical, microbiological and biological procedures showing the inhibitory effect of the compounds on the replication of herpes simplex viruses, types 1 and 2 (HSV-1 and HSV-2); and other herpes viruses, for example, varicella zoster virus (VZV), Epstein-Barr virus (EBV), equine herpes virus (EHV) and preudorabies virus (PRV).

Noteworthy is the fact that all of the aforementioned viruses are dependent on their own ribonuceotide reductase to synthesize deoxyribonucleotides for their replication. Although this fact may not be directly linked with the antiviral activity found for the present naphthalenes, the latter compounds have been shown so far to have antiviral properties against all viruses dependent on ribonucleotide reductase to synthesis is DNA for their replication.

In example 1 hereinafter, the inhibitory effect of an exemplary naphthalene is noted with respect to the specific inhibition of herpes ribonucleotide reductase. Noteworthy, in the connection with the specific inhibition of herpes ribonucleotide reductase, is the absence of such an effect on cellular ribonucleotide reductase activity required for normal cell replication.

A method for demonstrating the therapeutic effect of the naphthalenes is the guinea pig model for cutaneous herpes simplex viral infections; see S. Alenius and B. Oberg, Archives of Virology, 58, 277 (1978).

When a naphthalene of this invention, or one of its therepeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the naphthalene, chosen route of administration and standard biological practice. For topical administration, the naphthalene can be formulated in pharmaceutically accepted vehicles containing 0.1 to 10 percent, preferably 0.5 to 5 percent, of the active agent. Such formulations can be in the form of a solution, cream or lotion.

For systemic administration, the naphthalene of formula 1 is administered by either intravenous, subcutaneous or intramuscular injection, in compositions with pharmaceutically acceptable vehicles or carriers. For administration by injection, it is preferred to use the naphthalene in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described by G. H. Jones et al. in the previously noted U.S. patents, or they can be found in standard pharmaecutical texts, e.g. in "Remington's Pharmaceutical Sciences", 16th ed, Mack Publishing Company, Easton, Pa., 1980.

The dosage of the naphthalene will vary with the form of administration and the particular active agent chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the naphthalene is most desirably administered at a concentration level that will generally afford antivirally effective results without causing any harmful or deleterious side effects.

With reference to topical application, the naphthalene is administered cutaneously in a suitable topical formulation to the infected area of the body e.g. the skin or part of the oral or genital cavity, in an amount sufficient to cover the infected area. The treatment should be repeated, for example, every four to six hours until lesions heal. Healing results usually within 3 to 4 days. No contraindications have been observed.

With references to systemic administration, the naphthalene of formula 1 is administered at a dosage of 10 mcg to 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Although the formulation disclosed hereinabove are effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral interferons such as those disclosed by S. S. Asculai and F. Rapp in U.S. Pat. No. 4,507,281, Mar. 26, 1985.

Another aspect of this invention comprises a cosmetic composition comprising a herpes viral prophylactic amount of the naphthalene of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the naphthalene than corresponding pharmaceutical composition for topical application. A preferred range of the amount of the naphthalene in the cosmetic composition is 0.01 to 0.2 percent by weight.

The following example further illustrates this invention.

EXAMPLE 1

Specific Inhibition of HSV-1 Ribonucleotide Reductase by 6-Chloro-2,3-dimethoxy-1,4-naphthalenediol diacetate (1: $R^1$ and $R^2 = CH_3O$, $R^3 = 6\text{-}Cl$ and $W = CH_3$)

HSV-1 ribonucleotide reductase (partially purified) was obtained from quiescent BHK-21/C13 cells infected with strain F HSV-1 virus at 10 plague-forming units/cell as described by E. A. Cohen et al., J. Gen. Virol., 66, 733 (1985).

Hamster 96-V-2(600) ribonucleotide reductase (partially purified) was obtained from an overproducting strain of a Chinese hamster lung cell line as described by W. H. Lewis and P. R. Scinivasan, Mol. Cell Biol., 3, 1053 (1983).

Samples of the HSV-1 ribonucleotide reductase (65 $\mu g$ with a specific activity of 26 units per mg) were mixed with increasing concentrations of the test compound, i.e. the naphthalene noted in the title of this example, in a series of tubes. Ribonucleotide reductase activity was assayed by monitoring the reduction of cytidine diphosphate (CDP) as described by Cohen et al., supra. The standard reaction mixture, in a final volume of 60 $\mu l$, contained: 50 mM, N-2-hydroxyethylpiperazine-N'-2-ethanesulfonic acid (pH 7.8); 4 mM NaF, 30 mM DL-dithiothreitol (DTT); 1 mM bacitracin, 54 $\mu M$ CDP and 0.25 $\mu Ci$ of [$^3$H]CDP. After 30 minutes of incubation at 37° C., the reaction was stopped by immersing the tube in boiling water for 4 minutes. The precipitate was removed by centrifugation. Nucleotides in the supernatant were converted to nucleosides by enzymatic hydrolysis. The deoxyribonucleosides were subsequently separated from the ribonucleosides by ascending polyethyleneimine-celulose chromatography. One unit of ribonucleotide reductase is defined as the amount of enzymes generating 1 nmol of dCDP per hour under standard conditions. A control experiment (without the test compound) was run simultaneously. The results, shown in FIG. 1, are expressed as a percentage of the activity obtained in the controls.

As shown in FIG. 1, a fifty percent reduction of the HSV-1 ribonucleotide reductase activity was observed with 31 μM of the title compound, i.e. $IC_{50}=31$ μM. In a similar experiment wherein HSV-1 ribonucleotide reductase was replaced with hamster 96-V-2(600) ribonucleotide reductase (40 μg with a specific activity=38 units per mg) in the presence of adenosine triphosphate (4 mM) and magnesium chloride (11.5 mM), the $IC_{50}$ for the test compound was shown to be greater than 250 μM. Hence, the selective inhibition by the test compound of the viral ribonucleotide reductase over the cellular ribonucleotide reductase was demonstrated.

In the same manner, selective inhibition of HSV-1 ribonucleotide reductase activity is shown for 2,3-dimethoxy-1,4-1,4-naphthalenediol diacetate, 2,3,6-trimetoxy-1,4-naphthalenediol diacetate, 6-cyano-2,3-dimethoxy-1,4-naphthalenediol diacetate, 6-chloro-2,3-diethoxy-1,4-naphthalenediol dipropionate, and 6-chloro-2,3-dipropoxy-1,4-naphthalenediol diacetate.

The embodiments of the invention for which an exclusive property of privilege is claimed are defined as follows:

1. A method for preventing or relieving herpes viral infections in a mammal which comprises administering to the mammal an effective amount of a compound of formula 1

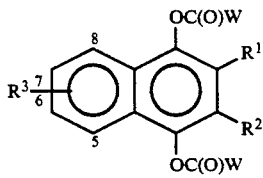

wherein:
$R^1$ and $R^2$ are lower alkoxy or lower alkylthio; $R^3$ is hydrogen, lower alkyl, lower alkoxy, optionally substituted phenyl, optionally substituted phenyl lower alkyl, optionally substituted phenyl alkoxy, amino, lower alkylamino, lower dialkylamino, halo, cyano, or $S(O)_nR$ wherein R is lower alkyl; optionally substituted phenyl; optionally substituted phenyl lower alkyl; and n is 0, 1 or 2; and W is alkyl of one of seven carbon atoms, or the pharmaceutically acceptable acid addition salts thereof.

2. A method of claim 1 wherein $R^3$ is hydrogen, lower alkyl, lower alkoxy, phenyl optionally substituted by one or more lower alkyl, lower alkoxy, halo, lower acyl, lower acyloxy, cyano, nitro or lower acylamino, phenyl lower alkyl optionally substituted by one or more lower alkyl, lower alkoxy, halo, lower acyl, lower acyloxy, cyano, nitro or lower acylamino, phenyl lower alkoxy optionally substituted by one or more lower alkyl, lower alkoxy, halo, lower acyl, lower acyloxy, cyano, nitro or lower acylamino, amino, lower alkylamino, lower dialkylamino, halo, cyano, $S(O)_nR$ wherein R is lower alkyl; phenyl optionally substituted by one or more lower alkyl, lower alkoxy, halo, lower acyloxy, cyano, nitro or lower acylamino; phenyl lower alkyl optionally substituted by one or more lower alkyl, lower alkoxy, halo, lower acyl, lower acyloxy, cyano, nitro or lower acylamino; and n is 0, 1 or 2, or the pharmaceutically acceptable acid addition salts thereof.

3. A method of claim 2 wherein the compound is represented by formula 1a

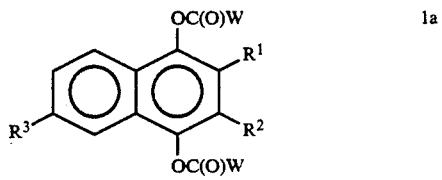

wherein $R^1$, $R^2$ $R^3$ and W are as defined in claim 2.

4. A method of claim 3 wherein $R^1$ and $R^2$ are each lower alkoxy.

5. A method of claim 3 wherein $R^3$ is hydrogen, bromo, chloro, fluoro or cyano.

6. A method of claim 3 wherein $R^1$ and $R^2$ are each lower alkoxy of one to four carbon atoms, $R^3$ is bromo, chloro, fluoro, cyano, methoxy, ethoxy, propoxy, 1-methylethyl, butoxy or 2-methylpropoxy, and W is an alkyl of one to five carbon atoms.

7. A method of claim 6 wherein the compound is 6-chloro-2,3-dimethoxy-1,4-naphthalenediol diacetate.

8. A method of claim 6 wherein the compound is 2,3-diemthoxy-1,4-naphthalenediol diacetate.

9. A method of claim 6 wherein the compound is 2,3,6-trimethoxy-1,4-naphthalenediol diacetate.

10. A method of claim 6 wherein the compound is 6-chloro-2,3-diethoxy-1,4-naphthalenediol dipropionate or 6-chloro-2,3-dipropoxy,1,4-naphthalenediol diacetate.

* * * * *